US005916599A

United States Patent [19]

Veneris et al.

[11] Patent Number: 5,916,599

[45] Date of Patent: Jun. 29, 1999

[54] APPARATUS FOR GENERATING GENERALLY UNIFORM COMPRESSION IN HIGH-VISCOSITY LIQUIDS

[75] Inventors: David C. Venerus; Mandana Kompani, both of Chicago, Ill.

[73] Assignee: Illinois Institute of Technology, Chicago, Ill.

[21] Appl. No.: 08/746,751

[22] Filed: Nov. 14, 1996

[51] Int. Cl.[6] .......... B29C 33/58

[52] U.S. Cl. .......... 425/96; 73/818; 425/95; 425/135; 425/DIG. 115

[58] Field of Search .......... 425/95, 107, DIG. 115, 425/96, 135; 73/818

[56] References Cited

U.S. PATENT DOCUMENTS

| | | | |
|---|---|---|---|
| H93 | 7/1986 | Matta et al. . | |
| 2,166,268 | 7/1939 | Simmons | 425/95 |
| 2,612,850 | 10/1952 | Marziani | 425/95 |
| 2,626,738 | 1/1953 | Nordquist | 425/95 |
| 2,762,859 | 9/1956 | Ostranger | 425/95 |
| 3,054,142 | 9/1962 | Hinderer et al. | 425/DIG. 115 |
| 3,069,727 | 12/1962 | Shramek | 425/DIG. 115 |
| 4,856,335 | 8/1989 | Tornberg . | |
| 4,913,868 | 4/1990 | Ito et al. | 249/113 |
| 4,992,487 | 2/1991 | Rao . | |
| 5,044,193 | 9/1991 | Fudacz . | |
| 5,260,017 | 11/1993 | Giles, Jr. . | |
| 5,269,190 | 12/1993 | Kramer et al. . | |
| 5,344,596 | 9/1994 | Hendry . | |
| 5,357,784 | 10/1994 | Collier . | |
| 5,415,536 | 5/1995 | Ohno . | |
| 5,431,784 | 7/1995 | Miyamoto et al. | 249/113 |
| 5,453,144 | 9/1995 | Kauffman et al. . | |
| 5,554,332 | 9/1996 | Schnallinger . | |

FOREIGN PATENT DOCUMENTS

| | | | |
|---|---|---|---|
| 1605203 | 11/1990 | U.S.S.R. | 73/818 |

OTHER PUBLICATIONS

M. Kompani, D.C. Venerus and B. Bernstein, Equibiaxial Extensional Flow (EBEX), a paper presented at the American Institute of Chemical Engineers 1995 Annual Meeting, Nov. 12–17, 1995.

M. Kompani, D.C. Venerus and B. Bernstein, Equibiaxial Extensional Flow of Polymer Melts, a paper presented at the American Institute of Chemical Engineers 1996 Annual Meeting, Nov. 13, 1996, Miami Beach, Florida.

M. Kompani, D.C. Venerus and B. Bernstein, Development and Evaluation of a Modified Lubricated Squeezing Flow Technique, a paper presented Aug. 18–23, 1996 at XII$^{th}$ Int'l. Congress on Rheology Meeting in Quebec City, Quebec, Canada, published in the Proceedings of the XIIth International Congress on Rheology, Quebec City, Quebec, Canada (1996).

J. Meissner, T. Raible and S.E. Stephenson, Rotary Clamp in Uniaxial and Biaxial Extensional Rheometry of Polymer Melts, Journal of Rheology, 25(1), 1–28 (1981).

S. Chatraei, and C.W. Macosko and H.H. Winter, Lubricated Squeezing Flow: A New Biaxial Extensional Rheometer, Journal of Rheology, 25(4), 433 (1981).

Secor, Robert Bruce, Ph.D., Operability of extensional rheometry by stagnation, squeezing, and fiber–drawing flows: Computer–aided analysis, viscoelastic characterization, and experimental analysis, Thesis, University of Minnesota, 1988.

*Primary Examiner*—James P. Mackey

*Attorney, Agent, or Firm*—Pauley Peterson Kinne & Fejer

[57] ABSTRACT

An apparatus for generating generally uniform compression forces over a film of a relatively low-viscosity liquid by passing the low-viscosity liquid through a porous plate, from an upstream face to a downstream face of the porous plate. The porous plate has a specified porosity and arrangement of the through holes or other pores that results in forming a uniform pressure through and uniform compression forces over a film of the low-viscosity liquid that is at or near the upstream face of the porous plate. The apparatus of this invention results in homogeneous deformation of a material, such as molten polymer, polymer solution, multiphase polymer systems, asphalts or foods.

13 Claims, 5 Drawing Sheets

APPARATUS FOR GENERATING GENERALLY UNIFORM COMPRESSION IN HIGH-VISCOSITY LIQUIDS

BACKGROUND OF THE INVENTION

1. Field of the Invention

This invention relates to an apparatus and method for generating essentially uniform compression in a relatively high-viscosity liquid, such as molten polymer, by squeezing the high-viscosity liquid between two parallel, porous plates which are each coated with a thin film of a relatively low-viscosity liquid having essentially uniform thickness and pressure, which are preferably maintained by continuously passing the low-viscosity liquid through the porous plate to a downstream face of the porous plate, at or near which the thin film is formed.

2. Description of Prior Art

Equibiaxial extensional (EBEX) flow relates to deformation of a material element by stretching the material equally in two directions while compressing the material in the third direction. Many polymer processing technologies, such as blow molding, compression molding and foamed polymer production, require simple and reliable methods for obtaining rheological flow data, which are not currently available.

Compression of molten polymers between unlubricated surfaces is conventional technology within the polymer processing industry and is often referred to as compression molding. In a compression molding process, a charge of molten polymer is positioned between two opposing solid surfaces that usually accommodate heat transfer from the molten polymer. A position of one of the two solid surfaces is normally fixed while a linear drive motor controls a variable position of the other solid surface. During the compression molding process, the distance between the two solid surfaces decreases over time.

In a compression molding process, the fixed solid surface is often mounted to a force transducer, so that it is possible to measure the force required to squeeze or compress the molten polymer. Measurement equipment, such as a displacement transducer, is often used to measure a distance between the opposing solid surfaces, under a given load. Compression molding is used to convert a molten polymer charge to a solid piece intermediate or final product that has a desired shape and thickness.

Compression molding technology produces nonhomogeneous deformation of the polymer material. Adhesion of the polymer to the solid surfaces results in shear deformation near the solid surfaces, thereby causing nonhomogeneous deformation, and nearly shear-free, or extensional, deformation in a central plane of the polymer material. Material near a central portion of the charge experiences relatively small deformations while material near an outer radial edge of the charge experiences relatively large deformations. Non-uniform deformation often produces different degrees of molecular orientation in compression molded pieces and thus non-uniform physical properties, as well as residual stresses that can diminish mechanical performance.

Unlubricated compression molding has been used to measure Theological properties of high-viscosity liquids, such as in connection with a conventional device referred to as a Williams Parallel-Plate Plastometer, which forms the basis for ASTM D926. The force or displacement resulting from a given displacement or force, respectively, can be measured and used to indicate rheological behavior of the polymer material. For Newtonian fluids, shear viscosity of the test material is simply related to the measured force and distance between the solid surfaces. However, for non-Newtonian fluids, such as molten polymers, there are no relatively simple relationships between measurable quantities, such as force and distance, and rheological properties. Thus, unlubricated compression technology is a relatively ineffective method for rheological analysis of relatively complex fluids.

Lubricated squeezing flow (LSF) methods, conventional technology, involve squeezing a viscous liquid between solid surfaces coated with a relatively thin film of a significantly lower viscosity liquid, such as a lubricant. The LSF method was developed for the purpose of generating equibiaxial extension in molten polymers. Lubricant films allow the molten polymer to slide past solid surfaces and thereby minimize shear flow in the melt, and thereby attempt to achieve uniform compression of the molten polymer. A lubricant film with a specified thickness is positioned between the molten polymer charge and the solid surfaces. The lubricant is usually a silicone oil which has a viscosity 1,000 to 100,000 times lower than the shear viscosity of the material, such as molten polymer melt.

In the known LSF method, as the material is compressed, lubricant flow from the film is driven by two types of flow: drag flow resulting from the flow of the polymer melt, and pressure-driven flow which is induced by the decreasing lubricant thickness. During compression of the melt, the lubricant film loses its effectiveness to prevent shear flow from occurring in the melt. The LSF method produces a relatively large pressure gradient over the lubricant film, causing the pressure in the lubricant to increase so that the force is no longer a simple function of the equibiaxial stress difference. The conventional LSF method is limited to relatively small deformations, such as where the equibiaxial Hencky strain is approximately 0.5. Thus, the LSF method is not particularly useful for the study of non-linear rheological behavior.

Other conventional methods have attempted to replace the lubricant loss over time in the LSF method, by injecting additional lubricant to the film through a single hole in a center of the plate. However, lubricant injection through a single hole in the center of the plate creates a substantial pressure gradient in the lubricant film and thus is not a viable solution to the lubricant thinning problem associated with conventional LSF technology.

The lubricant film between the two solid surfaces enhances but does not achieve uniformity of the pressure throughout the polymer material. However, there is an apparent need for an improvement to the existing LSF technology, the result of which generates a generally uniform pressure throughout the film positioned between the molten polymer charge and the solid surface.

SUMMARY OF THE INVENTION

It is one object of this invention to provide a method and apparatus for generating generally uniform compression forces over a film which is positioned between a displaceable surface and a molten polymer charge.

It is another object of this invention to provide a method and apparatus for passing the low-viscosity liquid through a porous plate.

It is another object of this invention to provide a method and apparatus for forming either a generally constant or a generally variable pressure gradient of the low-viscosity liquid at an upstream face of the porous plate.

The above and other objects of this invention are accomplished with a method and apparatus, each of which continuously delivers lubricant to a lubricant film established near a downstream face of the porous plate. By passing the lubricant through a plurality of through holes or pores within the porous plate, which are preferably positioned uniformly over a porous portion of the porous plate, generally uniform compression forces are generated over or through the film at or near the downstream face of the porous plate.

The apparatus of this invention preferably comprises two opposing porous plates, each having a film between opposing downstream faces and a charge of material, such as molten polymer, between opposing films. The uniform distribution of compression forces over a radius of each film results in uniform compression of the material. Because of the uniform compression forces, the material experiences homogenous deformation with significantly reduced or eliminated nonhomogeneous deformation.

A porous portion of the porous plate preferably has a porosity in a range of approximately 0.05 to approximately 0.2, and preferably approximately 0.1. Although the porous plate is preferably formed with a plurality of through holes extending from the upstream face to the downstream face, it is apparent that any other suitable structure can be used as long as the preferred porosity range is achieved.

The porous plate of this invention allows spatially-uniform flow of the lubricant through the holes or pores. By passing the lubricant through the porous plate, there is little or no tendency of the lubricant film to thin over time, and a generally or essentially uniform pressure is established over the radial or lateral direction of the film.

The apparatus and method according to this invention can be used to characterize rheological behavior of relatively high-viscosity liquids at deformation levels that are significantly higher, for example where the equibiaxial Hencky strain is approximately 1.5, than the conventional lubricated squeezing flow methods. According to the apparatus and method of this invention, it is possible to produce uniformly-oriented films and profiles of the high-viscosity material. The apparatus and method of this invention can be used with a relatively wide range of high-viscosity liquids, including molten polymers, polymer solutions, multiphase polymer systems, asphalts and foods. The apparatus and method of this invention can be used to test or process materials in constant force, constant stress, constant squeezing velocity and/or constant squeezing rate modes. Any conventional apparatus capable of controlled linear motion and force measurement can be easily retrofitted to accomplish the method of this invention, simply by replacing or modifying the conventional solid disks or plates with porous plates defined in this specification.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

Figure 1:
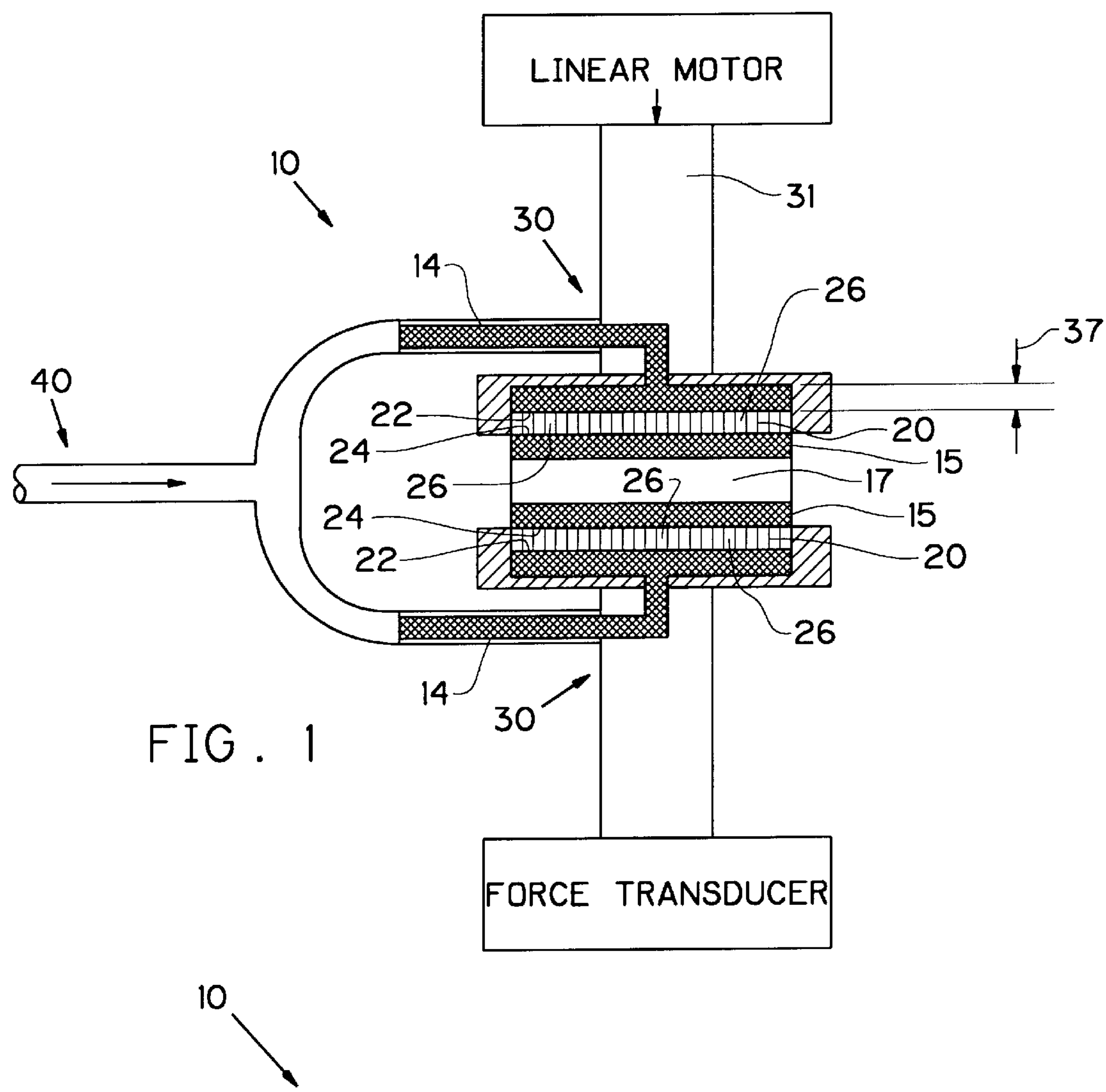
FIG. 1 is a schematic diagram showing a method and apparatus according to one preferred embodiment of this invention.

Referring to the schematic diagram shown in FIG. 1, apparatus 10 is used to generate generally uniform compression forces over film 15 of liquid 14. In one preferred embodiment according to this invention, liquid 14 is a relatively low-viscosity fluid, such as silicone oil having a viscosity of approximately 1,000 to approximately 100,000 times lower than a shear viscosity of material 17. In one preferred embodiment according to this invention, material 17 comprises molten polymer. As used throughout this specification and in the claims, the phrase molten polymer is intended to be interchanged with the word material, in the sense of the substance that is positioned between opposing films 15.

Figure 2:
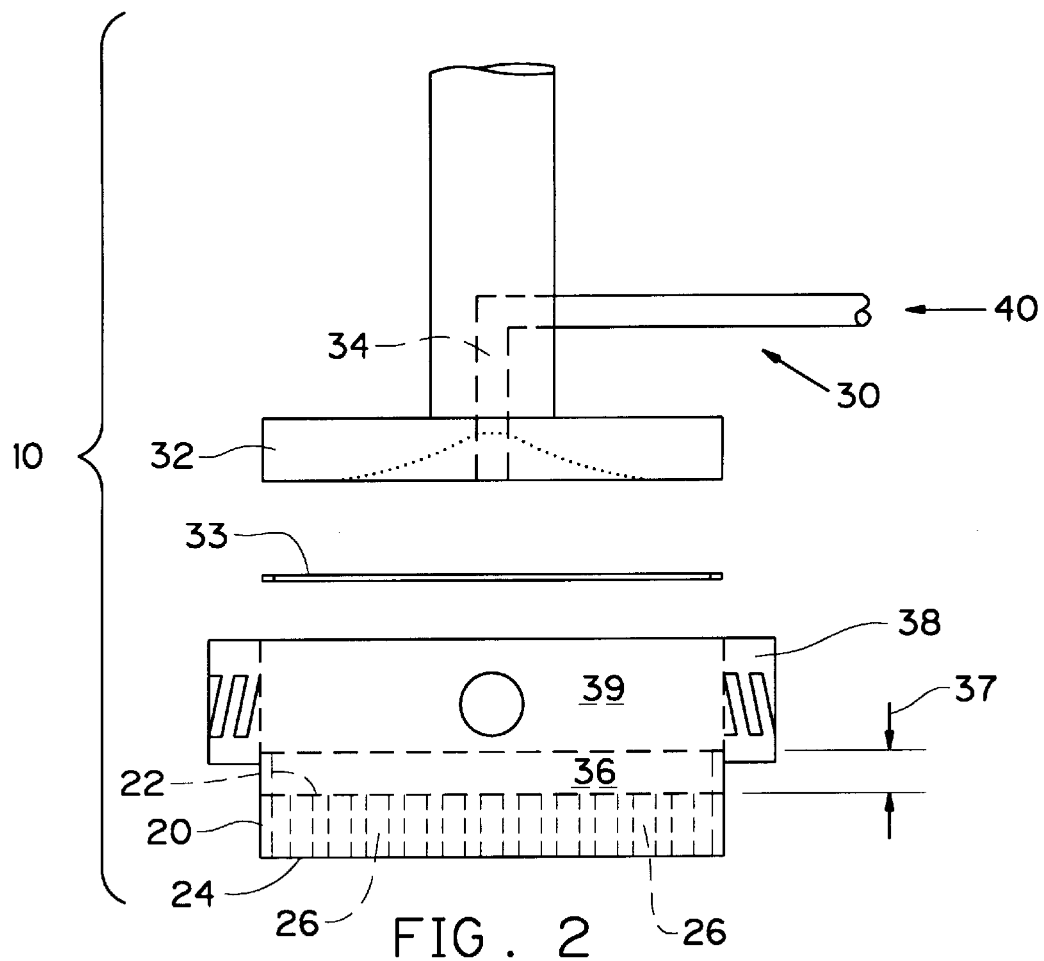
FIG. 2 is an exploded front view of a porous plate and an inlet means, according to one preferred embodiment of this invention.
Figure 3:
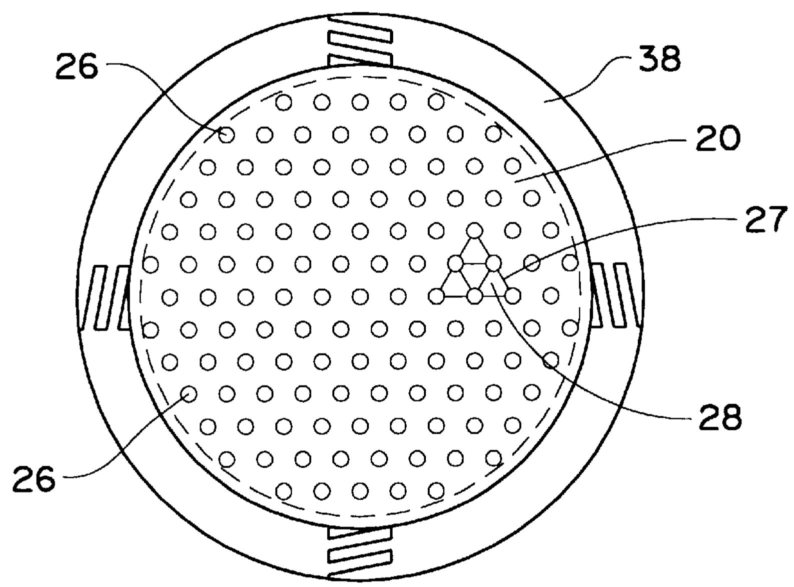
FIG. 3 is a bottom view of the porous plate shown in FIG. 2.

As shown in FIGS. 1–3, apparatus 10 comprises porous plate 20 which has upstream face 22 and downstream face 24. As used throughout this specification and in the claims, the words upstream and downstream are intended to relate to a direction that liquid 14 flows through apparatus 10.

Inlet means 30 distribute liquid 14 over upstream face 22 of porous plate 20. As shown in FIG. 1, inlet means 30 distributes liquid 14 over an entire region corresponding to a porous portion of porous plate 20. As used throughout this specification and in the claims the phrase a porous portion is intended to relate to a portion of porous plate 20 that has a porosity in a range of approximately 0.05 to approximately 0.2, and preferably approximately 0.1. Although as shown in FIGS. 2 and 3, the porous portion occupies nearly all of porous plate 20, it is apparent that porous plate 20 may also comprise a solid plate portion which may be used for structural support or the like. For purposes of this invention, the lateral area of the porous portion of porous plate should be approximately equal to or greater than a lateral area of material 17, so that film 15 entirely encompasses material 17 in a lateral direction, which is shown as a horizontal direction in FIGS. 1 and 2.

In one preferred embodiment according to this invention, the porous portion of porous plate 20 has a plurality of through holes 26 extending from upstream face 22 to downstream face 24. In one preferred embodiment according to this invention, each through hole 26 is positioned at a corresponding corner of one or more equilateral polygons which are uniformly arranged over porous plate 20. As shown in FIG. 3, the equilateral polygon is formed by multiple equilateral triangles 28. As used throughout this specification and in the claims, the phrase uniformly arranged is intended to relate to a patterned arrangement of polygonal shapes, such as shown in FIG. 3. It is apparent that the polygonal shape can be a square, a pentagon or any other suitable polygonal shape, and that the size of the holes and/or polygons may vary with radial or lateral position.

In another preferred embodiment according to this invention, porous plate 20 is constructed of a material that has an overall porosity in a range of approximately 0.05 to approximately 0.2. For example, porous plate 20 may be constructed of a material which has a surface roughness wherein an average largest material surface irregularity of porous plate 20 is at least approximately ten times smaller than an average smallest film thickness of film 15. Regardless of the structure of the porous portion of porous plate 20, achieving a porosity value in a range of approximately 0.05 to approximately 0.2, and preferably approximately 0.1, is the desired result. It is apparent that any other suitable structure or material of porous plate 20 can be used to achieve such porosity value and thus the desired results of this invention.

Inlet means 30 may comprise distributor plate 32, as shown in FIG. 2, which has inlet 34 and cavity 36. Delivery means 40 deliver liquid 14 to inlet means 30. Inlet 34 is in communication with delivery means 40 and cavity 36.

Cavity 36 distributes liquid 14 over upstream face 22 of the porous portion of porous plate 20. As shown in FIG. 1, depth 37 of cavity 36 is constant over a radius, shown in a horizontal direction in FIG. 1, of distributor plate 32. The constant dimension of depth 37 results in generally uniform compression forces over film 15. However, if it is desired to expose material 17 to a variable pressure along the radial or lateral direction of film 15, depth 37 may vary over at least a portion of the radius of distributor plate 32, as shown by the dashed lines in FIG. 2. By varying the dimension of depth 37, it is possible to apply generally uniform as well as variable compression forces over film 15, in the lateral direction.

As shown in FIG. 1, apparatus 10 comprises two opposing porous plates 20. Material 17 is sandwiched between two films 15 on opposite sides of material 17. Each film 15 is formed at downstream face 24 of the corresponding porous plate 20. FIG. 2 shows only one porous plate 20 whereas FIG. 1 shows two porous plates 20. It is apparent that a mirror image of the drawings shown in FIG. 2 can be used to visualize two opposing porous plate 20. Because the compression forces act towards each other, material 17 as shown in FIG. 1 is compressed.

As shown in FIG. 1, the method for compressing film 15 and generating generally uniform compression forces through film 15 requires passing liquid 14 through not just one but a plurality of pores in porous plate 20, from upstream face 22 to downstream face 24. Film 15 at or near downstream face 24 preferably has an aspect ratio in a range of approximately 0.05 to approximately 0.1. As used throughout this specification and in the claims, the phrase aspect ratio is intended to relate to a thickness of film 15 divided by a shortest lateral dimension of film 15. As shown in FIG. 1, the lateral dimension is in a horizontal direction.

Inlet means 30 and delivery means 40 deliver liquid 14 to both porous plates 20. Inlet means 30 may also comprise mounting shaft 31 which has a properly sized internal bore or conduit for accommodating flow of liquid 14 to cavity 36. It is apparent that any other suitable conduit or communication means can be used to distribute liquid 14 from delivery means 40 to cavity 36 and thus upstream face 22 of porous plate 20.

As shown in FIG. 2, inlet means 30 comprises housing 38 which has receptacle 39. Although FIG. 2 shows an exploded view, when distributor plate 32 is mounted or received within receptacle 39, a seal is formed so that liquid 14 does not escape from cavity 36 or housing 38. As shown in FIG. 2, gasket 33 can be mounted between distributor plate 32 and housing 38 in order to achieve a proper seal.

In one preferred embodiment according to this invention, porous plate 20 has a generally circular periphery and thus receptacle 39 has a generally circular cross section that accommodates the periphery of distributor plate 32. Although a circular periphery is preferred for distributor plate 32, receptacle 39 and/or porous plate 20, it is apparent that any other suitable mating shapes can be used between any required elements.

Figure 6:
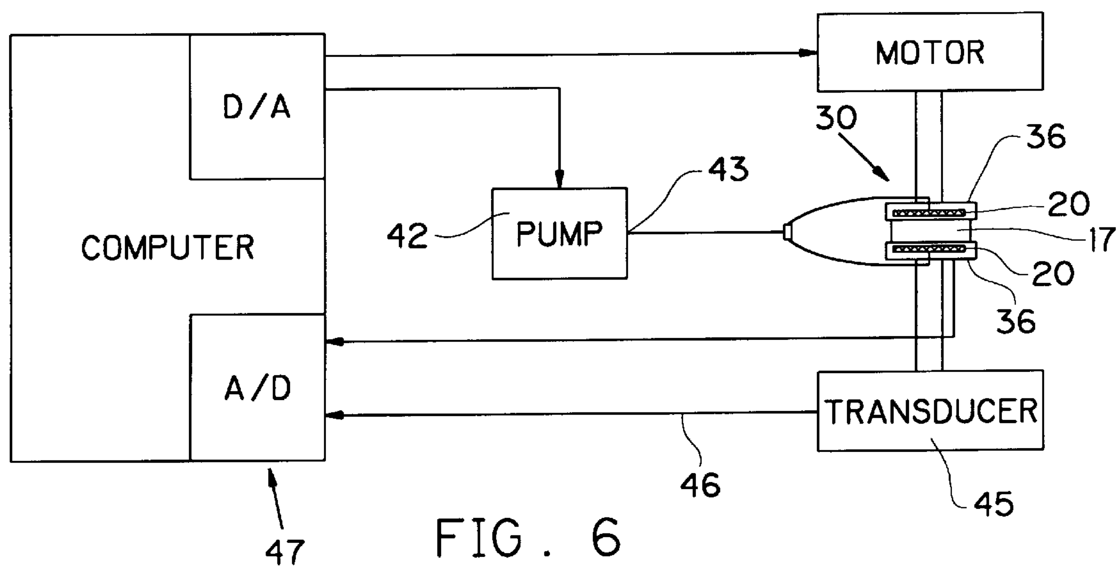
FIG. 6 is a schematic diagram of an apparatus and method, which includes a feedback control loop, according to another preferred embodiment of this invention.

In one preferred embodiment according to this invention, delivery means 40 comprise pump 42 or another suitable means for increasing and controlling a pressure of liquid 14 as it is delivered from delivery means 40. Pump 42 preferably has discharge 43 which is in communication with inlet means 30, as shown in FIG. 6. Delivery means 40 preferably but not necessarily delivers liquid 14 at flow conditions wherein at least one flow parameter, such as pressure, flowrate or the like, is constant.

In one preferred embodiment according to this invention, feedback means 47 are used to control the flow of liquid 14, for example as a function of feedback signal 46 which is detected and emitted from sensor 45. Sensor 45 can detect a force upon material 17, film 15 and/or liquid 14. It is also apparent that a displacement transducer can be used as sensor 45 to detect the distance that one porous plate 20 moves with respect to the other porous plate 20.

Figure 4:
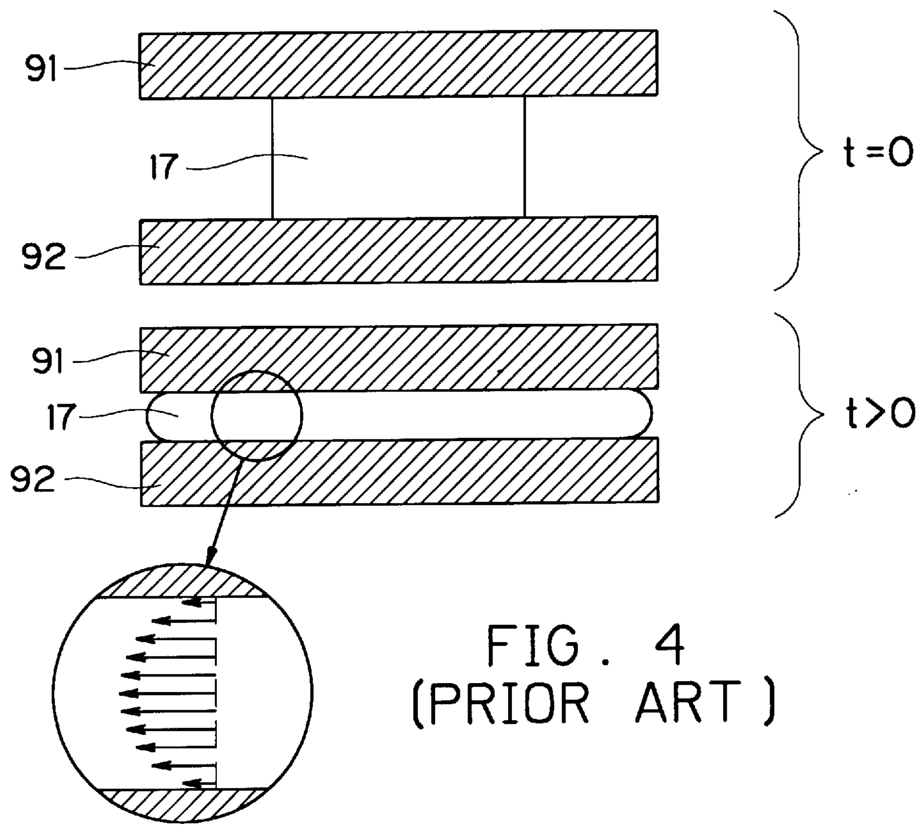
FIG. 4 is a schematic diagram showing a compression apparatus used according to a conventional compression molding process.
Figure 5:
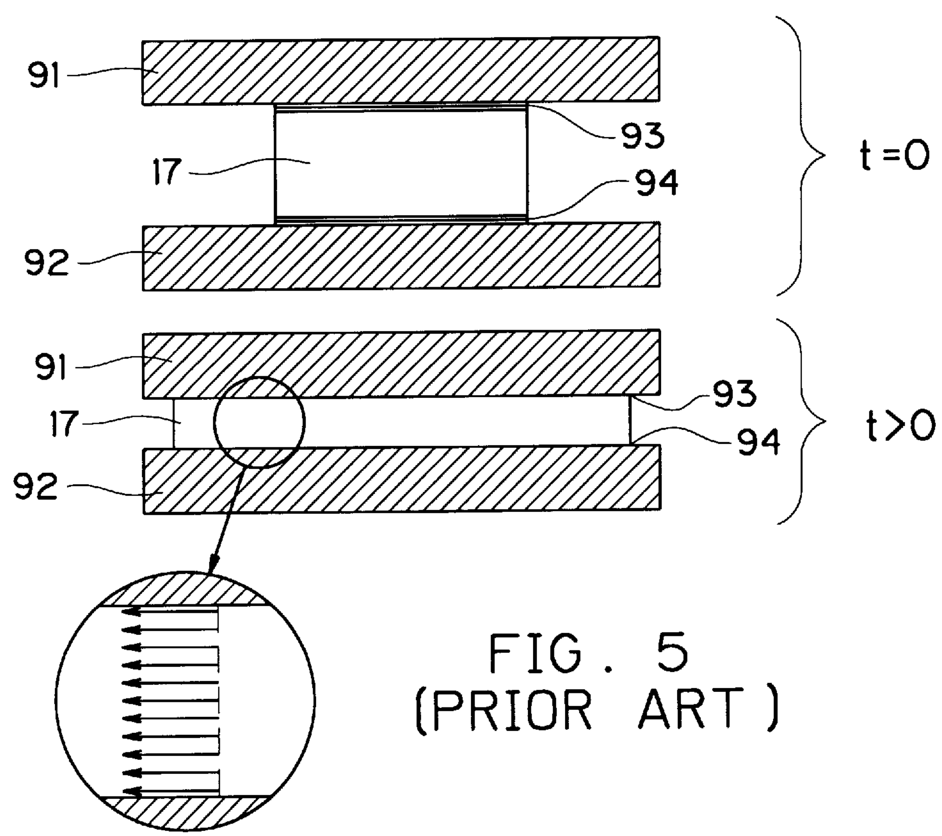
FIG. 5 is a schematic diagram of a conventional lubricated squeezing flow compression apparatus.

FIGS. 4 and 5 represent schematic diagrams of conventional methods. As shown in FIG. 4, material 17 is positioned between opposing solid disks 91 and 92 which are not porous. As material 17 is compressed, as shown in FIG. 4, it results in nonhomogeneous deformation. As shown in FIG. 5, material 17 is positioned between lubricant films 93, 94 and between solid disks 91, 92. Compression of material 17 results in more homogeneous deformation than the method shown in FIG. 4.

As shown in FIG. 2, housing 38 forms a step or shoulder upon which distributor plate 32 or gasket 33 rests and forms a seal. As shown in FIG. 2, according to one preferred embodiment of this invention, an upper half of housing 38 has an outer radius approximately 15% larger than an outer radius of porous plate 20. Set screws can be used to secure distributor plate 32 within receptacle 39.

The number, size and arrangement of through holes 26 may vary, depending upon the design parameters of the compression forces and pressure fields desired.

Figure 7:
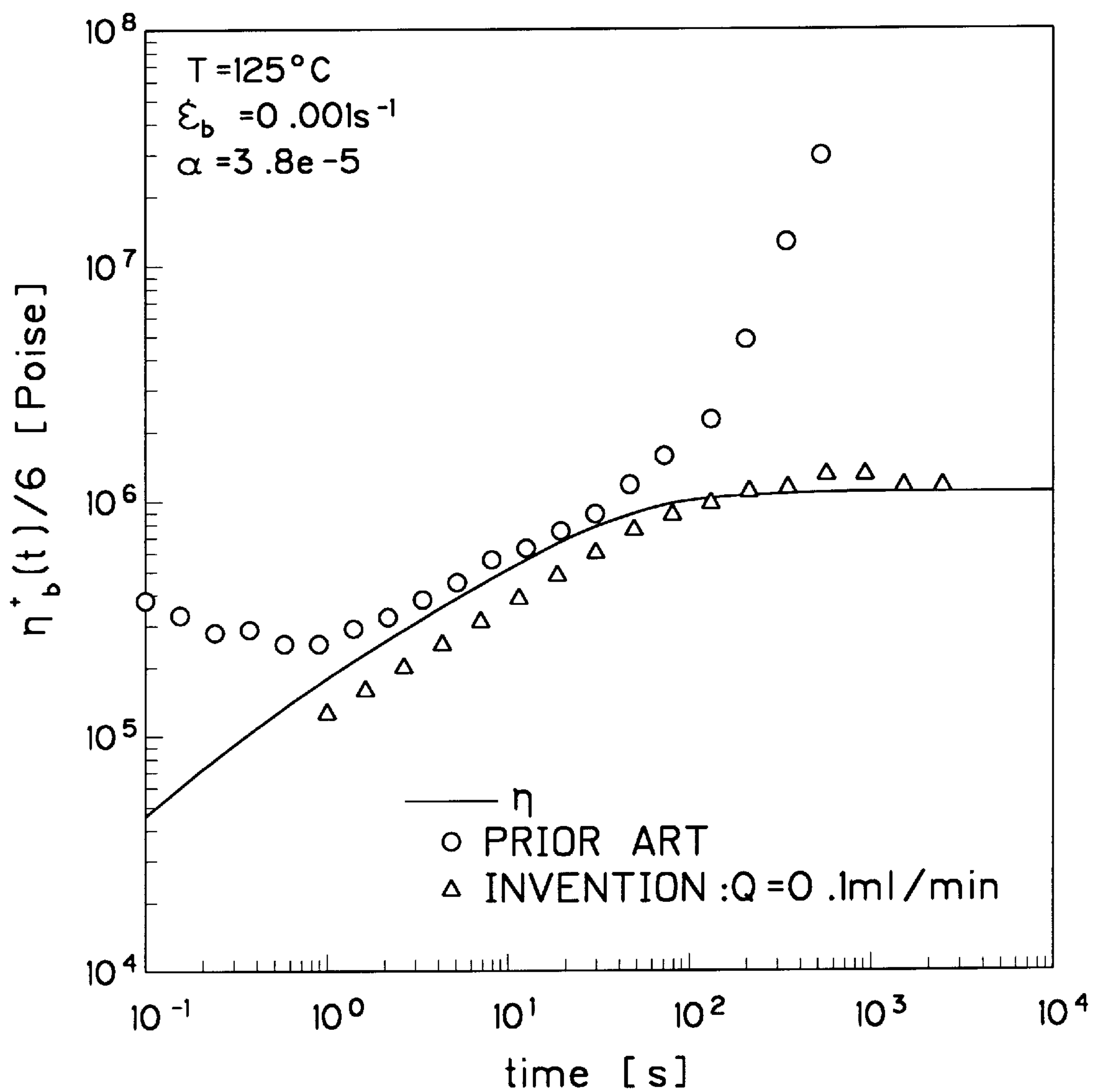
FIG. 7 is a graphical representation of data points and a curve showing the differences between viscosity and time for a conventional lubricated squeezing flow method and a method according to this invention.
Figure 8:
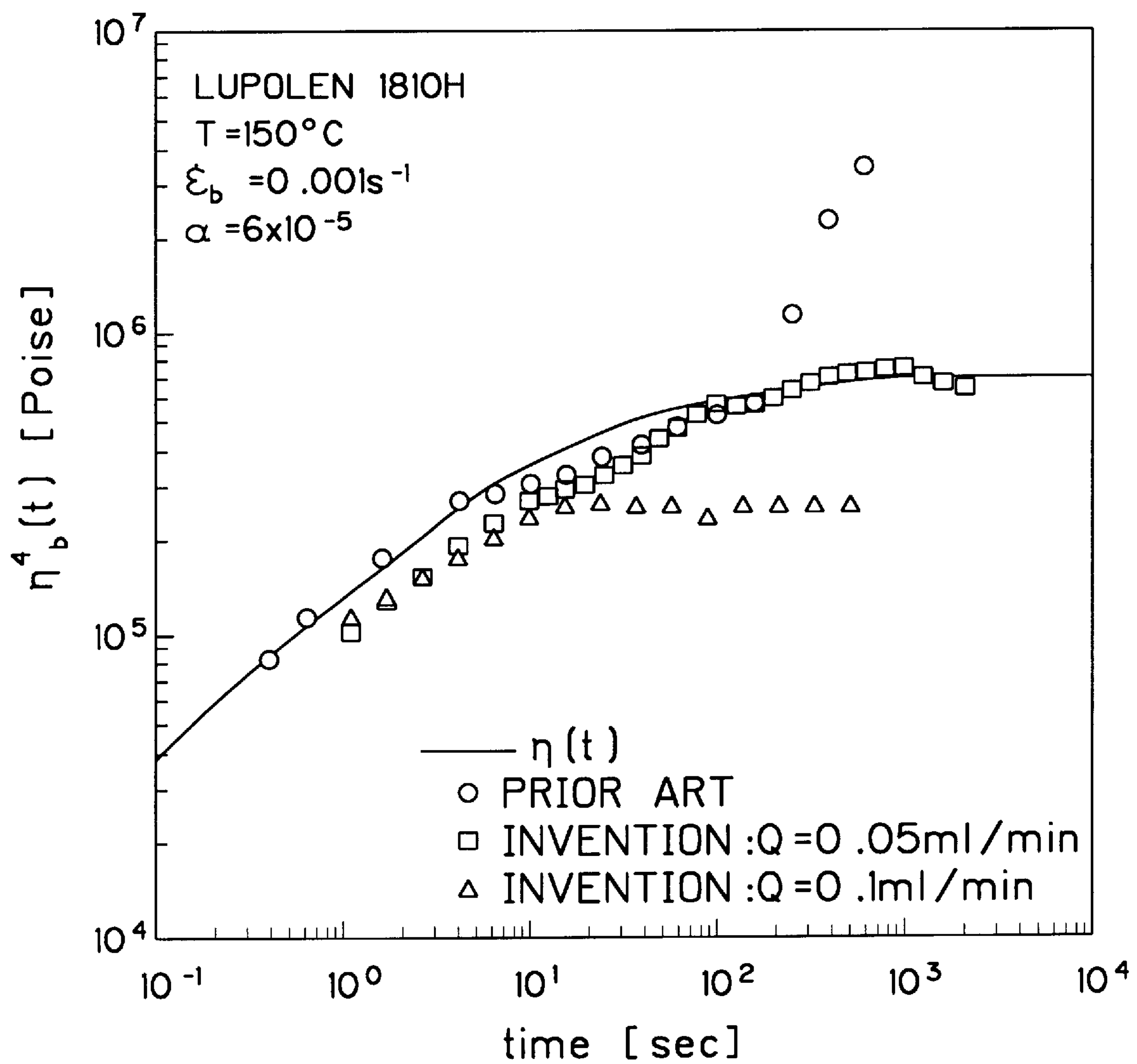
FIG. 8 is a graphical representation of data points and a curve showing the differences between viscosity and time for a conventional lubricated squeezing flow method and a method according to this invention.

FIGS. 7 and 8 show experimental data results, in graphical form, as compared to conventional lubricated squeezing flow (LSF) methods. The fluid data for each test is shown in the upper left corner of each of FIGS. 7 and 8. As shown in FIG. 7, the circled data points represent conventional LSF methods and the triangles represent data points according to the method of this invention, with the given flowrates Q. As shown in FIG. 7 it is apparent that the prior art LSF method deviates from an expected equibiaxial viscosity $\eta_b$, as shown by the solid line, at a Hencky strain of approximately 0.2, while the method according to this invention shows agreement up to a Hencky strain of approximately 1.5. It should be noted that the improvement corresponding to the method of this invention relates to greater than a factor of approximately ten in a compression ratio ($h/h_o$). The upper strain limit for the method according to this invention is due to limitations of the platform which was used, not due to a limitation of the method according to this invention. FIG. 8 shows similar results for different fluid parameters.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

We claim:

1. An apparatus for generating generally uniform compression forces over a film of a relatively low-viscosity liquid, the apparatus comprising:

a porous plate having an upstream face and a downstream face;

inlet means for distributing the low-viscosity liquid over said upstream face of said porous plate;

delivery means for delivering the low-viscosity liquid to the inlet means;

and a sensor for detecting and emitting a feedback signal corresponding to a sensed force upon said porous plate, and feedback means for controlling flow of said liquid as a function of said feedback signal.

2. An apparatus according to claim 1 wherein a porous portion of said porous plate has a porosity in a range of approximately 0.05 to approximately 0.2.

3. An apparatus according to claim 1 wherein a porous portion of said porous plate has a porosity of approximately 0.1.

4. An apparatus according to claim 1 wherein said porous plate has a plurality of through holes extending from said upstream face to said downstream face.

5. An apparatus according to claim 4 wherein said through holes are positioned at each of a plurality of corners of a plurality of equilateral polygons uniformly arranged over said porous plate.

6. An apparatus according to claim 1 wherein a porous portion of said porous plate is constructed of a material having a surface roughness wherein an average largest material surface irregularity of said material is approximately ten times smaller than an average smallest film surface thickness of said film.

7. An apparatus according to claim 1 wherein said inlet means comprise a distributor plate having an inlet in communication with said delivery means, a cavity in communication with said upstream face, and said inlet means in communication with said cavity.

8. An apparatus according to claim 7 wherein a depth of said cavity is constant over a radius of said distributor plate.

9. An apparatus according to claim 1 wherein said inlet means comprise a distributor plate mounted with respect to said porous plate and forming a cavity, said cavity having a depth dimension between said distributor plate and said porous plate, said depth dimension continuously varying over a radial direction of said distributor plate.

10. An apparatus according to claim 9 wherein said inlet means further comprise a housing secured with respect to said porous plate, said housing having a receptacle, and said distributor plate sealably received within said receptacle.

11. An apparatus according to claim 10 wherein said distributor plate has a generally circular periphery and said receptacle has a generally circular cross section.

12. An apparatus according to claim 1 wherein said delivery means comprise means for increasing and controlling a pressure of said low-viscosity liquid delivered from said delivery means, said pressure increasing and controlling means comprising a high-pressure discharge, and said high-pressure discharge in communication with said inlet means.

13. An apparatus according to claim 1 wherein said delivery means delivers the low-viscosity liquid such that at least one flow parameter of the low-viscosity liquid is constant.

* * * * *